US006409685B1

(12) United States Patent
Merzenich et al.

(10) Patent No.: US 6,409,685 B1
(45) Date of Patent: Jun. 25, 2002

(54) METHOD FOR IMPROVING MOTOR CONTROL IN AN INDIVIDUAL BY SENSORY TRAINING

(75) Inventors: Michael Mathias Merzenich, San Francisco; Nancy N. Byl, Oakland; William M. Jenkins, Pacifica, all of CA (US)

(73) Assignee: Scientific Learning Corporation, Oakland, CA (US)

( * ) Notice: Subject to any disclaimer, the term of this patent is extended or adjusted under 35 U.S.C. 154(b) by 0 days.

(21) Appl. No.: 09/470,047

(22) Filed: Mar. 21, 2000

Related U.S. Application Data (63) Continuation of application No. 08/970,339, filed on Nov. 14, 1997, now abandoned.

(51) Int. Cl.$^7$ .......................... A61B 5/103; A61B 5/117
(52) U.S. Cl. .......................... 600/587; 600/557; 601/23
(58) Field of Search ................................. 600/552, 554, 600/555, 557, 587; 601/23; 434/112, 113, 114; 607/48; 128/905, 925

(56) References Cited

U.S. PATENT DOCUMENTS

| | | | |
|---|---|---|---|
| 4,392,496 A | 7/1983 | Stanton | 607/48 |
| 4,467,815 A | 8/1984 | O'Brien et al. | 600/553 |

(List continued on next page.)

FOREIGN PATENT DOCUMENTS

| | | | |
|---|---|---|---|
| WO | WO 91/07133 | 5/1991 | A61B/5/103 |
| WO | WO 97/06730 | 2/1997 | A61B/5/0484 |

OTHER PUBLICATIONS

Srikatan S. Nagarajan et al., "Practice–Related Improvements in Somatosensory Interval Discrimination Are Temporarily Specific But Generalize across Skin Location, Hemisphere, and Modality," *The Journal of Neuroscience*, pp. 1559–1570 (1998).

(List continued on next page.)

*Primary Examiner*—Kevin Shaver
*Assistant Examiner*—Charles Marmor, II
(74) *Attorney, Agent, or Firm*—Beyer, Weaver & Thomas, LLP (57) ABSTRACT

A method and apparatus for implementing a training regimen which addresses motor control problems accompanied by sensory degradation. Accordingly, the training regimen is applicable to motor control disorders associated with a variety of different causes, including traumatic injury, disease, aging and gradual "occupational" type injury. For example, in an individual suffering from repetitive strain injury (RSI), the disabling motor control problems are often accompanied by sensory problems. These sensory problems appear to be caused over time by harmful attended rapid repetitive movements resulting in undesirable changes in the somatosensory, proprioceptive and/or kinesthetic ability of the affected regions of the individual. The present invention hypothesizes that repetitive delivery of simultaneous or nearly simultaneous afferent sensory inputs, under attended conditions of high cognitive drive, results in a learning-induced integration of the representation of the individuality of otherwise differentiable parts of the subjects thereby degrading the sensory feedback loop necessary for normal motor control. What started out as a degradation of the sensory feedback capability, essential for proper motor control, eventually manifests over time as a motor control problem. Thus, motor control problems which are accompanied by sensory degradation can be alleviated by a regimen of remedial re-differentiating sensory training of the affected regions of the individual. Accordingly, the training regimen differentially stimulates two locations within the afflicted portion of the individual. Feedback from the individual indicates the degree of difficulty the individual has in sensing differentially between the two locations. The stimulation is then adapted to the individual based on the feedback. Adaptation includes increasing the distance between the two locations and/or changing the spectral or temporal characteristics of the stimuli.

33 Claims, 6 Drawing Sheets

U.S. PATENT DOCUMENTS

| | | | |
|---|---|---|---|
| 4,690,142 A | 9/1987 | Ross et al. | 128/905 |
| 4,763,666 A | 8/1988 | Strian et al. | 600/555 |
| 4,811,742 A | 3/1989 | Hassel et al. | 600/554 |
| 5,002,065 A | 3/1991 | LaCourse et al. | 600/552 |
| 5,020,542 A | 6/1991 | Rossmann et al. | 600/554 |
| 5,022,407 A | 6/1991 | Horch et al. | 600/552 |
| 5,027,828 A | 7/1991 | Kovacevic et al. | 600/552 |
| 5,078,152 A | 1/1992 | Bond et al. | 600/587 |
| 5,191,896 A | 3/1993 | Gafni et al. | 600/555 |
| 5,195,532 A | 3/1993 | Schumacher et al. | 128/739 |
| 5,230,345 A | 7/1993 | Curran et al. | 600/552 |
| 5,333,618 A | 8/1994 | Lekhtman et al. | 600/554 |
| 5,337,757 A | 8/1994 | Jain et al. | 600/592 |
| 5,363,859 A | 11/1994 | Tuckett et al. | 600/552 |
| 5,381,805 A | 1/1995 | Tuckett et al. | 600/552 |
| 5,410,472 A | 4/1995 | Anderson | 482/9 |
| 5,522,386 A | 6/1996 | Lerner | 600/557 |
| 5,533,514 A | 7/1996 | Lavigne et al. | 600/557 |
| 5,673,703 A | 10/1997 | Fisher et al. | 600/552 |
| 5,692,906 A | 12/1997 | Corder | 434/156 |
| 5,719,561 A | 2/1998 | Gonzales | 340/7.51 |
| 5,720,711 A | 2/1998 | Bond et al. | 601/23 |
| 5,792,212 A | 8/1998 | Weijand | 600/554 |
| 5,797,854 A | 8/1998 | Hedgecock | 600/554 |
| 5,806,522 A | 9/1998 | Katims | 600/554 |
| 5,830,158 A | 11/1998 | Zanakis | 600/595 |
| 5,919,149 A | 7/1999 | Allum | 600/595 |
| 5,980,429 A | 11/1999 | Nashner | 482/8 |
| 6,063,046 A | 5/2000 | Allum | 600/595 |

OTHER PUBLICATIONS

Lederman, S. J. (1974). Tactile roughness of grooved surfaces: The touching process and effects of macro–and microsurface structure. *Perception & Psychophysics*, 16 (2), 385–395.

Vega–Bermudez, F., Johnson, K. O., & Hsiao, S. S. (Mar., 1991). Human Tactile Pattern Recognition: Active Versus Passive Touch, Velocity Effects, and Patterns of Confusion. *Journal of Neurophysiology*, 65 (3), 531–546.

Craig, J. C., & Rhodes, R. P. (1992). Instrumentation & Techniques, Measuring the error of localization. *Behavior Research Methods, Instruments, & Computers*, 24 (4), 511–514.

Evans, P. M., & Craig, J. C. (1992). Response competiion: A major source of interference in a tactile identification task. *Perception & Psychophysics*, 51 (2), 199–206.

Evans, P. M., & Craig, J. C. and Rinker, M. A. (1992). Perceptual processing of adjacent and nonadjacent tactile nontargets. *Perception & Psychophysics*, 52 (5), 571–581.

Carey, L. M., Matyas, T. A., Ph.D., and Oke, L. E. MappSc. Sensory Loss in Stroke Patients: Effective Training of Tactile and Proprioceptive Discrimination. *Archives of Physical Medicine and Rehabilitation*, vol. 74, (Jun., 1993) pp. 602–611.

Craig, J. C. (1993). Anomalous sensations following prolonged tactile stimulation. *Neuropsychologia*, 31, (3), 277–291.

Dannenbaum R. M., & Jones, L. A. (Apr.–Jun., 1993). The Assessment and Treatment of Patients Who Have Sensory Loss Following Cortical Lesions. *Journal of Hand Therapy*, 130–138.

Vickery, R. M., Morley, J. W., & Rowe, M. J. (1993). The role of single touch domes in tactile perception. *Experimental Brain Research*, 93, 332–334.

Yekutiel, M., and Guttman, E. (1993). A Controlled trial of the retraining of the sensory function of the hand in stroke patients. *Journal of Neurology, Neurosurgery, and Psychiatry*, 56, 241–244.

Byl, N. N., Merzenich, M. M., & Jenkins, W. M.,. A primate genesis model of focal dystonia and repetitive strain injury: I. Learning–induced dedifferentiation of the representation of the hand in the primary somatosensory cortex in adult monkeys. *American Academy of Neurology*, 47, (Aug., 1996) 508–520.

Byl, N., Wilson, F., Merzenich, M., Melnick, M., Scott, P., Oakes, A., McKenzie, A., (Apr., 1996). Sensory Dysfunction Associated With Repetitive Strain Injuries of Tendinitis and Focal Hand Dystonia: A Comparative Study. *JOSPT*, 23, (4), 234–244.

Kramis, R., C., Roberts, W. J., & Gillette, R. G., (Oct., 1996). Non–nociceptive Aspects of Persistent Musculoskeletal Pain. *JOSPT*, 24, (4), 255–266.

Byl, N. N., Merzenich, M. M., Cheung, S., Bedenbaugh, P., Nagarajan, S. S., & Jenkins, W. M., (Mar., 1997). A primate model for studying focal dystonia and repetitive strain injury: Effects on the primary somatosensory cortex. *Physical Therapy*, 77, (3), 269–284.

Patentec Search Report, Jun. 15, 1998.

Thomas Elbert et al., Alteration of digital representations in somatosensory cortex in focal hand dystonia, (Nov. 16, 1998), *NeuroReport*, vol. 9, No. 16, pp. 3571–3575.

Byl, Nancy, Ph.D., and Topp, Kimberly S., Ph.D., Focal Hand Dystonia, (Jan., 1998), *Physical Therapy Case Reports*, vol. 1, No. 1, pp. 39–52.

Bruno Kopp et al., Plasticity in the motor system related to therapy–induced improvement of movement after stroke, (Mar., 1999), NeuroReport, vol. 10, No. 4, pp. 807–810.

James J. DiCarlo et al., Structure of Receptive Fields in Area 3b of Primary Somatosensory Cortex in the Alert Monkey, (Apr. 1, 1998), *The Journal of Neuroscience*, pp. 2626–2645.

J.R. Phillips et al., Spatial pattern representation and transformation in monkey somatosensory cortex, (Feb., 1988), *Proc. Natl. Acad. Sci.*, Neurobiology, vol. 85, pp. 1317–1321.

METHOD FOR IMPROVING MOTOR CONTROL IN AN INDIVIDUAL BY SENSORY TRAINING

This is a Continuation application of application Ser. No. 08/970,339 filed on Nov. 14,1997 now abandoned.

BACKGROUND OF THE INVENTION

1. Field of the Invention

The present invention relates to alleviation of motor control problems. More particularly, the present invention relates to a computerized method of improving motor control in an individual via somatosensory, proprioceptive and/or kinesthetic sensory training.

2. Description of the Related Art

Motor control problems in individuals are rooted in a variety of different causes, including traumatic injury, disease, aging and gradual "occupational" type injury. If the affected individual is motivated enough to participate in a rehabilitative training program, recovery is possible and is highly dependent on the quantity and quality of the training program.

In cases where motor control problems in individuals are caused by traumatic injury to or disease of the muscle(s) and/or related nerve(s), depending on the extent of injury to the nerve(s), such individuals may or may not experience a corresponding loss of sensory ability. Typical causes of injuries include trauma, stroke, aneurysm, and invasive surgery. Examples of diseases include meningitis and cancer. Historically, regardless of whether the motor control problem is accompanied by a loss of sensory ability, these individuals have been treated with strengthening, flexibility, conditioning and motor retraining techniques, with limited success.

Often, motor control problems are not caused by injury or disease, but are associated with a gradual degradation of motor control over time. Examples include work-induced focal dystonia, Alzheimer, torticollis, cerebral palsy, multiple sclerosis and movement disorders in Parkinson's Disease, Huntington's Chorea, and in other progressive neurological illnesses.

A common origin of focal dystonia is as a component of a repetitive strain injury (RSI) which appears to be the result of attended rapid movements repeated over a relatively long period of time. Generally, these potentially harmful rapid movements occur at a frequency at or below about 100 milliseconds. Typical symptoms of RSI include loss of motor control and involuntary movements of the affected hand, foot, limb or neck of the affected individual.

One example of rapid movements involves musicians and typists, or other skilled manual workers who are required to repeatedly execute rapid alternating movements, e.g., to produce trills and keyboard strokes, to perform a particular assembly line task, etc. When executed repeatedly over a period of time, these rapidly alternating movements put one at risk for RSI.

In a study involving musicians with focal hand dystonia, subjects shared common histories of increased practice and of extended, demanding performances under stressful conditions prior to the onset of the disabling symptoms. While most of their biomechanical tests were normal, there was a clear asymmetry in passive finger spread in the central digits, forearm and shoulder rotation. These motor control limitations forced some of the musicians to adopt compensatory awkward end range postures which in some cases caused inflammatory problems of the capsule, ligaments, tendons and fascia, i.e., typical RSI symptoms.

Potentially harmful rapid movements also include rapid simultaneous movement of adjacent portions of a limb which can otherwise be controlled independently, e.g., when multiple digits of one hand, are opened and closed rapidly. In one study involving primates, attended repetitive activities, under the conditions of high cognitive drive were conducted over a three month period.

In one experiment, the monkeys placed a hand on two bars that passively spread apart within 20 milliseconds. The monkeys were required to squeeze the palm and the digits against a hand piece while maintaining close contact with the hand piece during the entire movement trial. The hand piece opened between one and seven times per trial for a total of 1300 repetitions in a training session. In a second experiment, the monkeys were required to repetitively squeeze the hand piece. A successful trial required full hand contact, 80 grams of force, squeezed for 500–1000 milliseconds. Each successful trial was rewarded, with approximately 400 trials completed per training session.

Following about eight weeks of training, despite continued rewards, these monkeys began to avoid training. For example, they began to decrease the time and repetitions of the sessions and would lick their thumbs or hand as if it was painful. They also developed some compensatory strategies such as reducing the intensity of the grasp on the hand piece and/or using an arm pulling instead of the required hand squeezing strategy. When training was continued, symptoms of an occupationally induced RSI emerged in all five subject monkeys after approximately five weeks. Four of the five monkeys showed signs of inefficient motor control of the required tasks as well as in other non-trial movements such as retrieving food. The fifth monkey developed the most serious dystonic movements in the fourth digit of the trained hand.

Hence, it appears that subjects who suffer from RSI can develop a form of focal dystonia, a disorder of motor control manifested in a specific context during rapid skilled, attended movements. Unlike traumatic injury patients, most RSI subjects experience a slow onset of symptoms, often beginning as a feeling of awkwardness, fatigue, or impaired timing or force. Eventually, if the potentially harmful repetitive movements are continued, the degradation of motor control is often preceded, paralleled or followed by painful inflammatory problems of the capsule, ligaments, tendons and fascia.

Conventional RSI treatment such as strengthening, flexibility, conditioning and motor retraining exercises appear to offer only temporary relief. This is because the conventional treatments are directed at the symptoms and but do not attempt to identify nor address the source of the problem. As a result, despite rest and conventional treatment, the motor control problems and any accompanying inflammation often return as soon as the subjects attempt to resume the repetitive movements.

In view of the foregoing, there are desired improved techniques for addressing motor control problems accompanied by sensory degradation using a training regimen that addresses the root of the motor control problem and not just the symptoms of motor control. Such a regimen should offer a comprehensive solution thereby enabling the affected individuals to substantially regain normal motor control over the longer term.

SUMMARY OF THE INVENTION

The present invention provides a method and apparatus for implementing a training regimen that addresses motor control problems accompanied by sensory degradation. Accordingly, the training regimen is applicable to motor control disorders associated with a variety of different causes, including traumatic injury, disease, aging and gradual "occupational" type injury.

For example, in an individual suffering from repetitive strain injury (RSI), the disabling motor control problems are often accompanied by sensory problems. These sensory problems do not appear to result from a peripheral nerve injury or disease. Instead, it appears that over time harmful attended rapid repetitive movements cause undesirable changes in the somatosensory, proprioceptive and/or kinesthetic ability of the affected regions of the individual. Briefly, somatosensory inputs include the light and deep tactile inputs, stretch, slow and rapidly adaptive tactile and vibratory tactile inputs. Proprioception and kinesthesia involve inputs from muscles, joints and skin contributing to movement control and locational sense control, respectively.

These sensory problems manifest themselves in a variety of symptoms. While some individuals with hand dystonias are able to differentiate light touch from deep touch, or sharp from dull pressure, they are unable to accurately interpret tactile cues through the skin, muscle afferents or tendons relative to location. In other words, these individuals appear to retain the ability to sense gross inputs but are unable to differentiate between the afflicted regions, i.e., there is a loss in sensory differentiation of the afflicted regions. For example, some individuals have difficulty determining which finger was stimulated, or whether one or more fingers were receiving the stimulus.

In some individuals, the motor control disorder includes involuntary motor control: co-contraction of flexors and extensors, inaccuracy, weakness, fatigue, loss of coordination and involuntary dystonic movements, e.g., when a hand touches a specific target interface. As a result, the individual can no longer perform tasks that require fine motor coordination of the affected portions.

The present invention hypothesizes that repetitive delivery of simultaneous or nearly simultaneous afferent sensory inputs, under attended conditions of high cognitive drive, results in a learning-induced integration of the representation of the individuality of otherwise differentiable parts of the subjects thereby degrading the sensory feedback loop necessary for normal motor control. Hence, the learning-induced progressive destruction of the otherwise highly differentiable representations of digit skin and of muscle afferent inputs involved with the muscles controlling the fingers is the root cause of the degradation of hand movement control. In other words, what started out as a degradation of the sensory feedback capability, essential for proper motor control, eventually manifests over time as a motor control problem.

As discussed above, motor control problems can also be the result of nerve injury or disease. In such cases, where nervous regeneration is possible, recovery can be enhanced by addressing the sensory degradation problem.

Thus, motor control problems accompanied by sensory degradation due to input integration or nerve damage/ disease, can be alleviated by a regimen of remedial re-differentiating sensory training of the affected regions of the individual. Accordingly, the training regimen of the present invention differentially stimulates two locations within the afflicted portion of the individual. Feedback from the individual indicates the degree of difficulty the individual has in sensing differentially between the two locations. The stimulation is then adapted to the individual based on the feedback. Adaptation includes increasing the distance between the two locations and /or changing the spectral or temporal characteristics of the stimulation.

The present invention is effective and long lasting because the training regimen addresses a root cause of the motor control problem and not just the symptoms. These and other advantages of the present invention will be apparent upon reading the following detailed descriptions and studying the various figures of the drawings.

BRIEF DESCRIPTION OF THE DRAWINGS

FIGS. 4–7B illustrate several embodiments of the stimulator useful for administering the training regimen of FIGS. 3A and 3B.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order to avoid unnecessarily obscuring the present invention.

Figure 1:
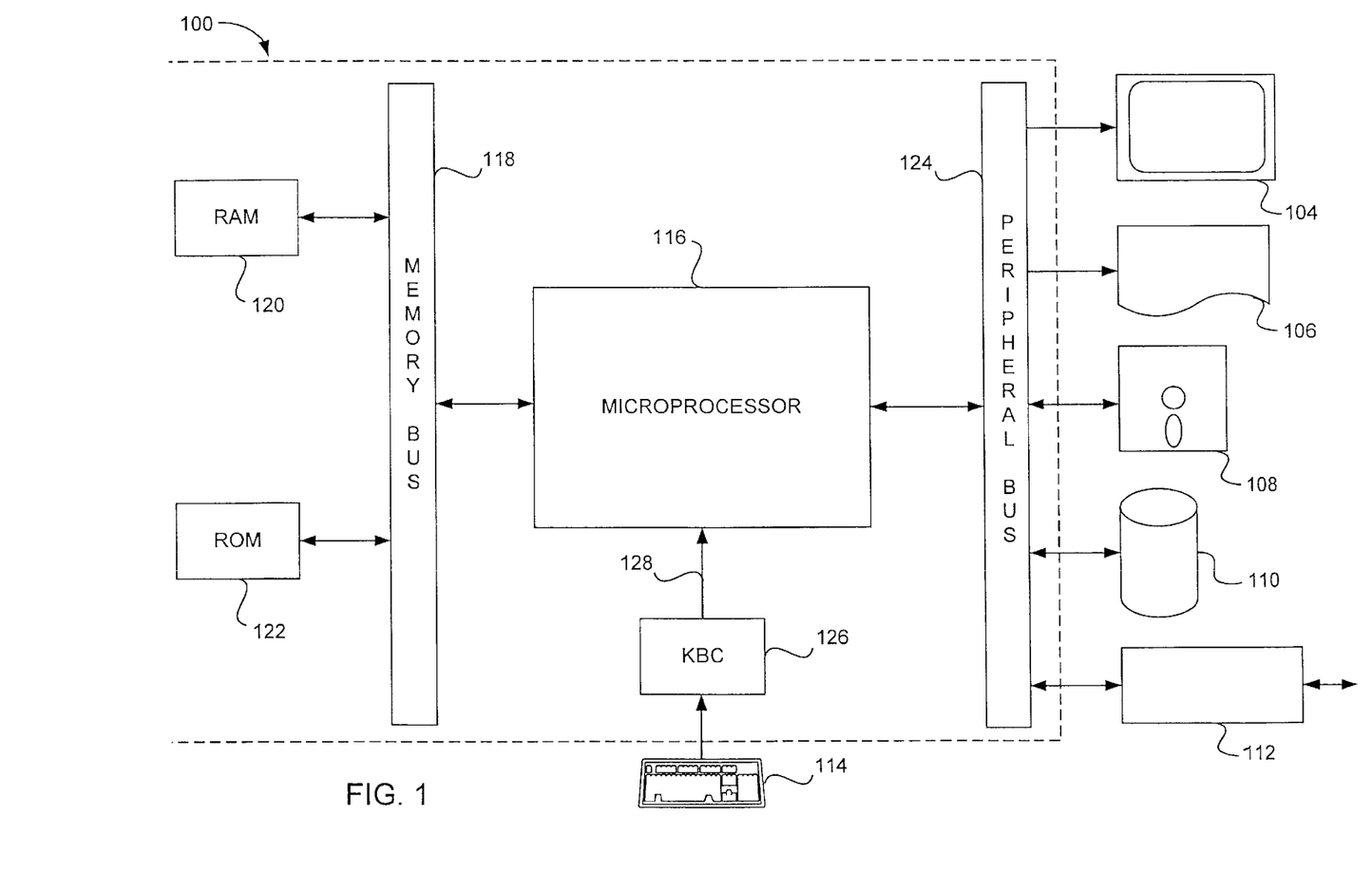
FIG. 1 is a block diagram of an exemplary computer system for practicing the invention.

FIG. 1 is a block diagram of an exemplary computer system 100 for practicing the various aspects of the present invention. Computer system 100 includes a display screen (or monitor) 104, a printer 106, a floppy disk drive 108, a hard disk drive 110, a network interface 112, and a keyboard 114. Computer system 100 includes a microprocessor 116, a memory bus 118, random access memory (RAM) 120, read only memory (ROM) 122, a peripheral bus 124, and a keyboard controller 126. Computer system 100 can be a personal computer (such as an Apple computer, e.g., an Apple Macintosh, an IBM personal computer, or one of the compatibles thereof), a workstation computer (such as a Sun Microsystems or Hewlett-Packard workstation), or some other type of computer.

Microprocessor 116 can be a general purpose digital processor which controls the operation of computer system 100. Microprocessor 116 can be a single-chip processor or can be implemented with multiple components. Using instructions retrieved from memory, microprocessor 116 controls the reception and manipulation of input data and the output and display of data on output devices.

Memory bus 118 is used by microprocessor 116 to access RAM 120 and ROM 122. RAM 120 is used by microprocessor 116 as a general storage area and as scratch-pad memory, and can also be used to store input data and processed data. ROM 122 can be used to store instructions or program code followed by microprocessor 116 as well as other data.

Peripheral bus 124 is used to access the input, output, and storage devices used by computer system 100. In the described embodiment(s), these devices include display screen 104, printer device 106, floppy disk drive 108, hard disk drive 110, and network interface 112. Keyboard controller 126 is used to receive input from keyboard 114 and send decoded symbols for each pressed key to microprocessor 116 over bus 128.

Display screen 104 is an output device that displays images of data provided by microprocessor 116 via peripheral bus 124 or provided by other components in computer system 100. Printer device 106 when operating as a printer provides an image on a sheet of paper or a similar surface. Other output devices such as a plotter, typesetter, etc. can be used in place of, or in addition to, printer device 106.

Floppy disk drive 108 and hard disk drive 110 can be used to store various types of data. Floppy disk drive 108 facilitates transporting such data to other computer systems, and hard disk drive 110 permits fast access to large amounts of stored data.

Microprocessor 116 together with an operating system operates to execute computer code and produce and use data. The computer code and data may reside on RAM 120, ROM 122, or hard disk drive 120. The computer code and data could also reside on a removable program medium and loaded or installed onto computer system 100 when needed. Removable program mediums include, for example, CD-ROM, PC-CARD, floppy disk and magnetic tape.

Network interface circuit 112 is used to send and receive data over a network connected to other computer systems. An interface card or similar device and appropriate software implemented by microprocessor 116 can be used to connect computer system 100 to an existing network and transfer data according to standard protocols.

Keyboard 114 is used by a user to input commands and other instructions to computer system 100. Other types of user input devices can also be used in conjunction with the present invention. For example, pointing devices such as a computer mouse, a track ball, a stylus, or a tablet can be used to manipulate a pointer on a screen of a general-purpose computer.

The present invention can also be embodied as computer readable code on a computer readable medium. The computer readable medium is any data storage device that can store data which can be thereafter be read by a computer system. Examples of the computer readable medium include read-only memory, random-access memory, magnetic data storage devices such as diskettes, and optical data storage devices such as CD-ROMs. The computer readable medium can also be distributed over a network coupled computer systems so that the computer readable code is stored and executed in a distributed fashion.

The training regimen of the present invention is applicable to individuals whose motor control problems are accompanied by a degradation of differential sensory inputs in the somatosensory, proprioceptive and/or kinesthetic sensory domains. As discussed above, the causes of the motor control problems in such individuals are varied and include traumatic injury, disease, aging, and motor control disorders which appear to be induced by gradual destructive "learning" over time such as repetitive strain injury (RSI). However, although the training regimen is applicable to a wide range of motor control problems, the regimen is described below using an exemplary motor control impaired individual who is afflicted with RSI, hereinafter referred to as the RSI individual.

The present invention hypothesizes that motor control problems in the RSI individual start out as a progressive destructive integration of sensory representations of the afflicted portions of the RSI individual, resulting in the gradual loss of differential motor control. In turn the loss of motor control leads to awkward end range postures which increases the risk for painful inflammatory problems of the capsule, ligaments, tendons and fascia.

One explanation for the origin of the underlying integration problem is that the brain of most primates is unable to separately process and hence differentiate sensory input information that is not separated by more than about forty to about two hundred milliseconds in time. In time, the continued bombardment of stereotyped inputs in this time domain begins to destructively retrain the brain. Unable to distinguish these rapid and nearly simultaneous inputs as distinct inputs, in accordance with brain plasticity hypotheses of the present invention, the brain begins to integrate these inputs representationally, over time. Eventually, the RSI individual retrains his/her brain into integrating these inputs. Fine details of sensory inputs that were formerly represented separately are now represented only in a degraded, integrated form. As a result, what started out as a degradation of the sensory feedback capability, essential for proper motor control, eventually manifests over time as a motor control problem.

In view of the above hypothesis, the sensory retraining regimen of the present invention is effective because voluntary primate motor control is basically a closed loop control system with a sensory feedback loop. Accordingly, when the sensory feedback loop is degraded, a corresponding degradation of the motor control function is expected. Conversely, conventional treatment regimens that do not address the feedback loop and only attempt to correct the motor control function are inefficient because they do not directly address the degradation of the sensory loop, and are unlikely to result in a lasting satisfactory resumption of normal motor control.

Figure 2:
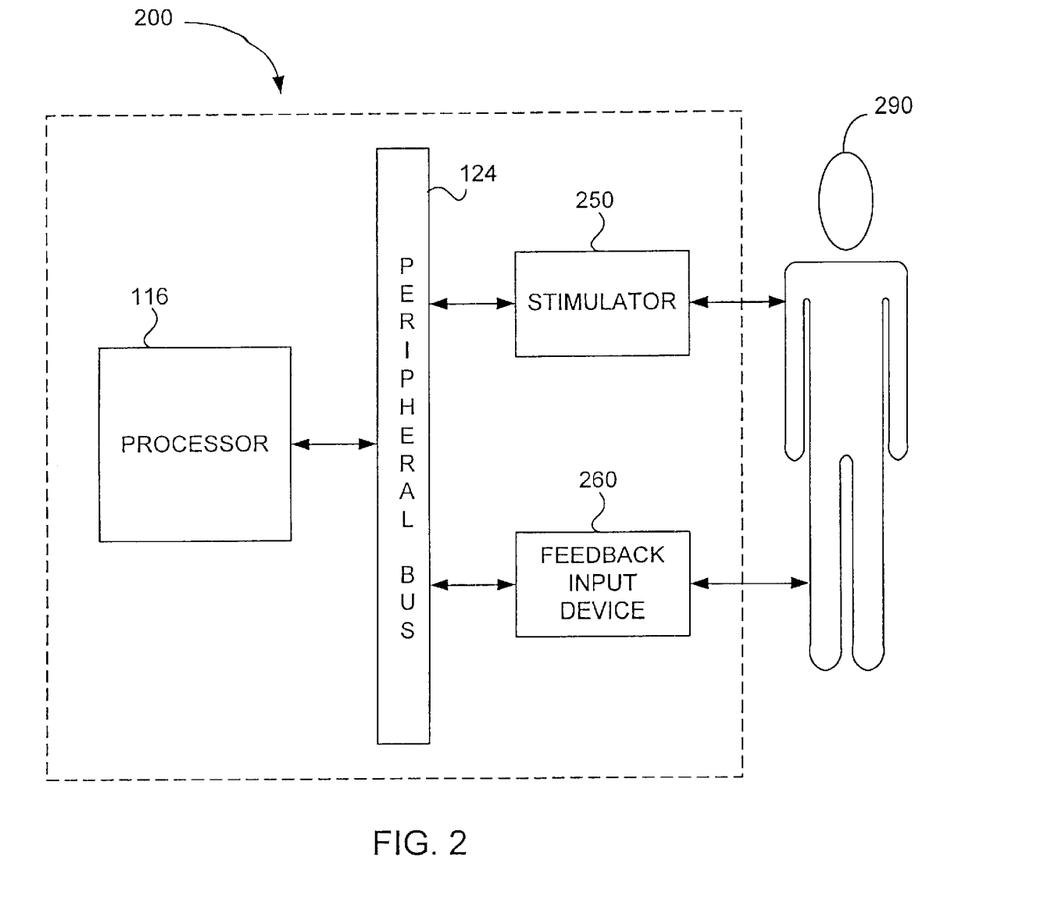
FIG. 2 is a block diagram showing an exemplary hardware environment for implementing the various aspects of the present invention.

As shown in FIG. 2, an exemplary sensory trainer 200 provides a platform for administering a training regimen for an RSI individual 290 afflicted with motor control problem accompanied by sensory degradation (MCSD). Trainer 200, also referred to herein as stimulation system 200, includes processor 116, peripheral bus 124, a stimulator 250 and an input device 260.

Sensory inputs useful for the training regimen include somatosensory, proprioceptive and/or kinesthetic sensory inputs. Somatosensory inputs include the light and deep tactile inputs, stretch, slow and rapidly adaptive tactile, and vibratory tactile inputs. Proprioception and kinesthesia involve inputs from muscles, joints and skin contributing to movement control and locational sense control, respectively. Accordingly, sensory stimulus provided by stimulator 250 shall include one or more of the following:

Light touch (e.g., meaningful/meaningless form and textual detection)

Deep touch (slowly adapting and rapidly adapting fibers)

Vibration (different frequencies and intensities)

Proprioception of position (e.g. mid range and extremes of motion)

Temperature (cold to hot)

Stretch (golgi tendon organs, muscle spindles)

Figure 3A:
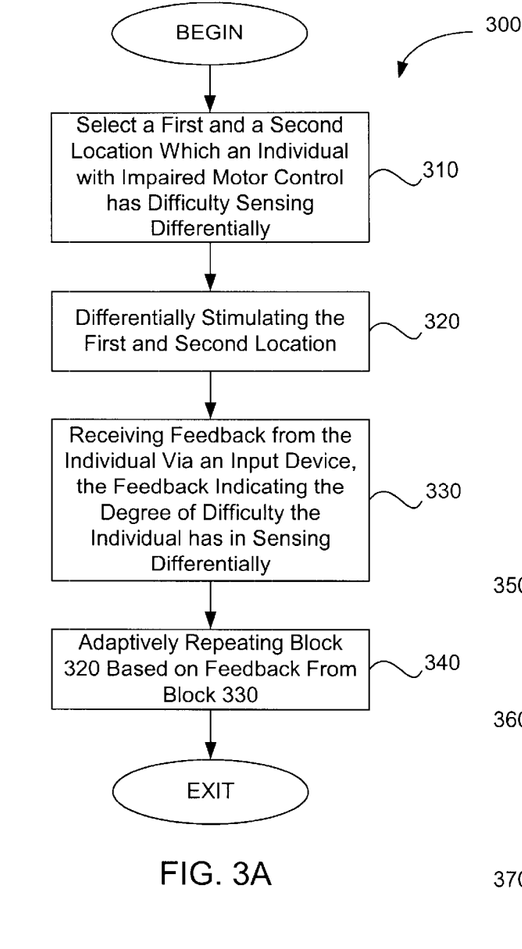
FIGS. 3A and 3B are flowcharts illustrating the remedial re-differential sensory training regimen of the present invention.
Figure 3B:
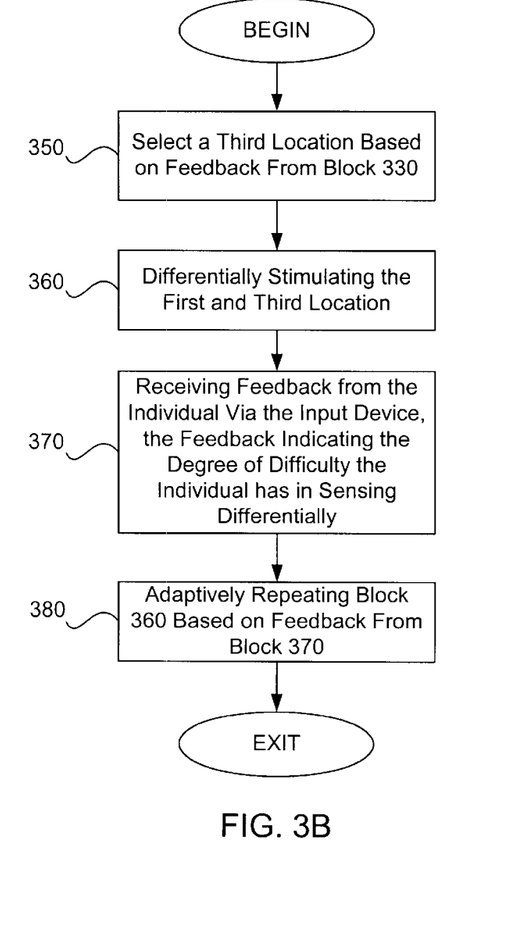

FIGS. 3A and 3B are flowcharts illustrating the training regimen of the present invention. Referring also to FIG. 2, since the extent of the motor control problem will vary from one individual to another, the first step of the regimen is a diagnostic of an individual, e.g., individual 290, to select a suitable pair of locations for starting the sensory training. Accordingly, in step 310, an initial first and second location is selected for which individual 290 may have difficulty sensing differentially. Stimulator 250 begins to provide stimuli differentially between the first and second location (step 320).

In the preferred embodiment, individual 290 provides feedback indicating the degree of difficulty that he/she is experiencing in differentiating the stimuli between the first and the second location (step 330). Feedback from individual 290 can be in the form of tactile responses, e.g., depressing a pressure sensitive switch under a finger, and/or via verbal responses, e.g., speaking into a microphone. In some embodiments, visual cues for guiding individual 290 during the sensory training regimen can be provided by monitor 104. In other embodiments of stimulation system 200, visual cues for individual 290 may not be necessary, thereby eliminating the need for monitor 104.

Depending on the feedback from step 330, stimulator 250 adaptively varies the stimuli at the first and second location (step 340). The stimuli can be modified or varied temporally and/or spectrally. Modifiable parameters include intensity, spectral frequency, duration, temporality and spatial orientation.

Referring to FIG. 3B, if individual 290 is unable to differentiate or has great difficulty differentiating stimuli between the first and second location, a third location is selected, wherein the distance between the first and third location is greater than the distance between the first and the second location. Conversely, if individual 290 can easily differentiate stimuli between the first and second location, a third location is selected, wherein the distance between the first and third location is smaller than the distance between the first and second location. (Step 350).

In step 360, differential stimuli resumes with the first and third location. Again, depending on the feedback from individual 290 indicating his/her degree of difficulty in differentiating between the first and third location, stimulator 250 adaptively varies the stimuli on the first and third location (steps 370, 380).

In accordance with the brain plasticity principles, substantial improvement in the motor control ability of individual 290, attributable to the training regimen of the present invention, should be observable after about 10 to 30 days of consistent re-differential sensory training. The training regimen should include about 1000 to 3000 stimuli exercises distributed into daily sessions, each session approximately one to two hours in duration, with rest breaks. Ideally, the training monitored by a physical therapist for compliance and safety reasons. Further, since the brain of individual 290 is plastic and is continually learning, continuing the training regimen beyond the initial training period should result in further improvement in motor control.

If individual 290 has an accompanying peripheral nerve injury, the sensory discrimination training is modulated according to the return of sensation along with positioning and maintenance of normal postures and normal movement despite any isolated paralysis. Accordingly, the present training regimen should positively influence the rate of recovery of sensation.

In accordance with another aspect of the invention, the training regimen provides motivation to encourage compliance. For example, the training regimen may be disguised as a treasure hunt implemented as a multimedia game. The clues for the treasures may be textural. Correct identification of the texture advances individual 290 to the next sequence of the treasure hunt.

As discussed above, there are numerous ways of providing stimuli to individual 290, including somatosensory, proprioceptive and/or kinesthetic stimuli. In the following detailed description of exemplary implementations of stimulator 250, the primary stimuli to be provided by stimulator 250 is textural/tactile stimuli and to a lesser extent pressure and/or positional stimuli.

Figure 4:
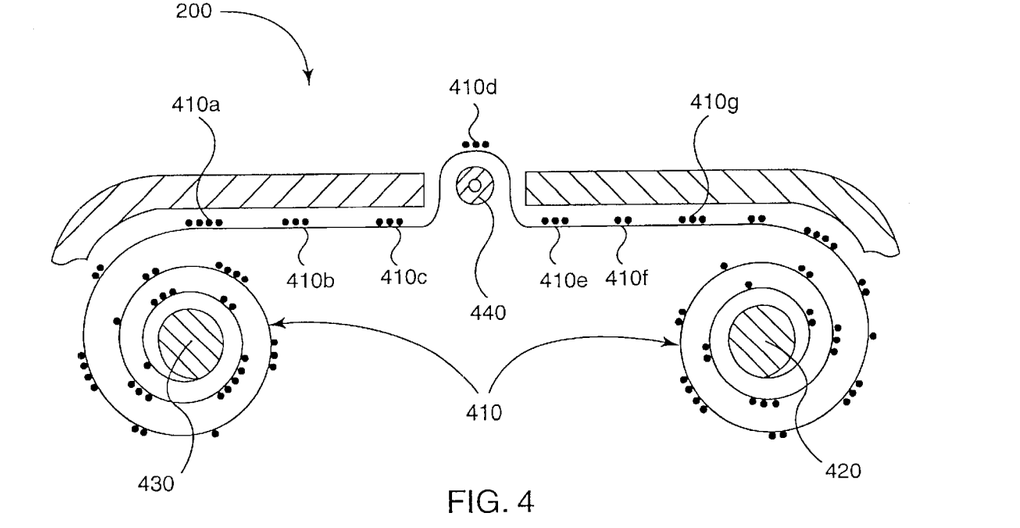

Referring now to FIG. 4, stimulation system 200 includes a pair of spools 420, 430 which accommodate a tape 410. Tape 410 has embossed patterns 410*a*, 410*b*, 420*c*, 410*d*, 410*e*, 410*f*, and 410*g* distributed on one surface. Examples of suitable embossed patterns include Braille characters, alpha numeric characters and textural patterns.

Tape 410 is presented to individual 290 over a roller 440. In addition to supporting tape 410, roller 440 may also provide pressure, e.g., forced feedback to individual 290. Patterns 410*a*, 410*b*, 420*c*, 410*d*, 410*e*, 410*f*, and 410*g* may be presented at various speeds. The presentation. can either be a smooth continuous flow or one stop frame (pattern) at a time as in a movie projector. Individual 290 places a finger on top of the exposed portion 410*d* of tape 410 and is required to differentiate patterns 410*a*, 410*b*, 420*c*, 410*d*, 410*e*, 410*f*, and 410*g*.

Figure 5:
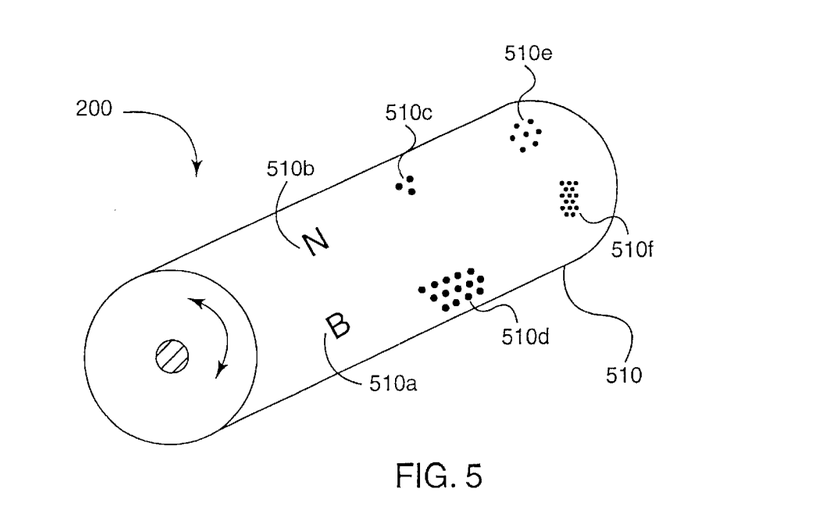

Alternatively, as shown in stimulation system 200 of FIG. 5, patterns 510*a*, 510*b*, 520*c*, 510*d*, 510*e* and 510*f* are embossed on a drum 510. With this setup, a relatively large embossed pattern, e.g., pattern 510*d*, can be presented to individual 290. As such, it is possible to provide stimuli to several locations simultaneously.

Figure 6:
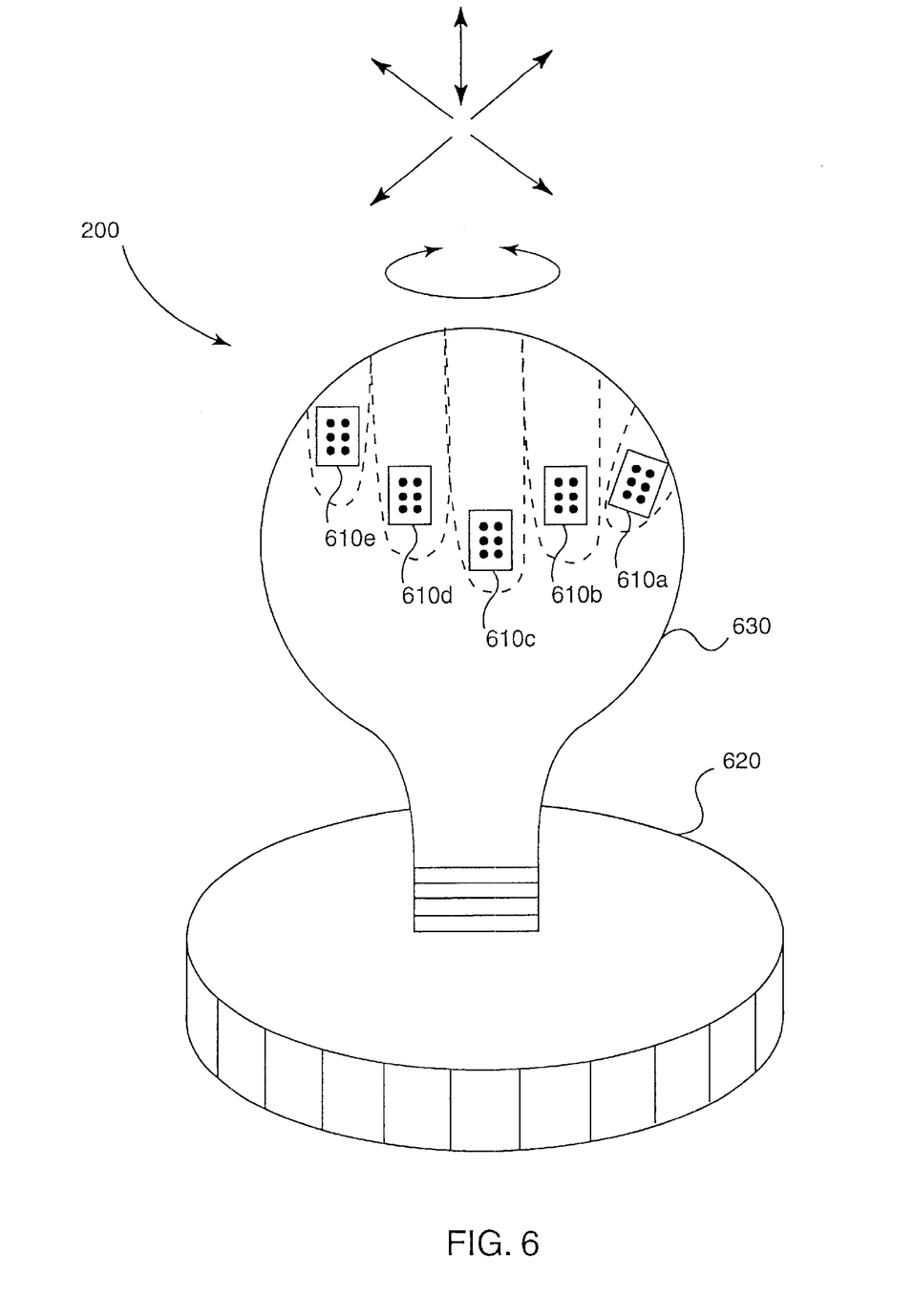

FIG. 6 illustrates yet another embodiment of stimulation system 200 which includes a ball 630, i.e., stimulator 250, operatively coupled to a base 620, i.e., input device 260. In this example, individual 290 places a hand over ball 630, with finger pads over stimuli pads 610*a*, 610*b*, 610*c*, 610*d* and 610*e* located on ball 630. Stimuli pads 610*a*, 610*b*, 610*c*, 610*d* and 610*e* may be electromechanical or piezoelectric driven pads with pins protruding from the pads when actuated. Suitable Braille pads include the Cell 16 pads of the PowerBraille Product Family and are available from Telesensory Corp. of Sunnyvale, Calif. (see website "www.telesensory.com").

Individual 290 provides positional feedback to stimulation system 200 by manipulating ball 630 relative to base 620, in a manner not unlike that of manipulating a joystick of a multimedia game. Several degrees of movement and rotation can be provided by system 200. Optional feedback can be provided by individual via pressure sensitive switches located below the respective stimuli pads 610*a*, 610*b*, 610*c*, 610*d* and 610*e*.

Figure 7A:
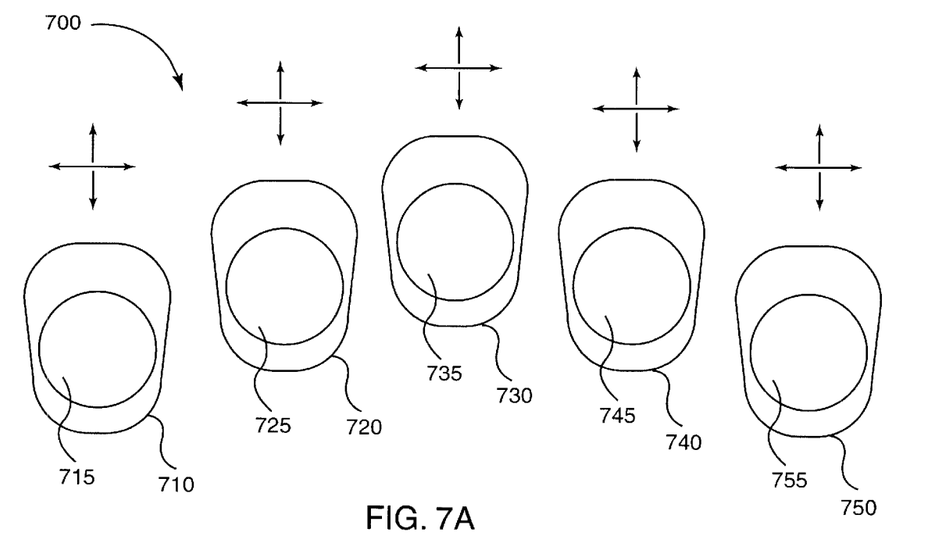
Figure 7B:
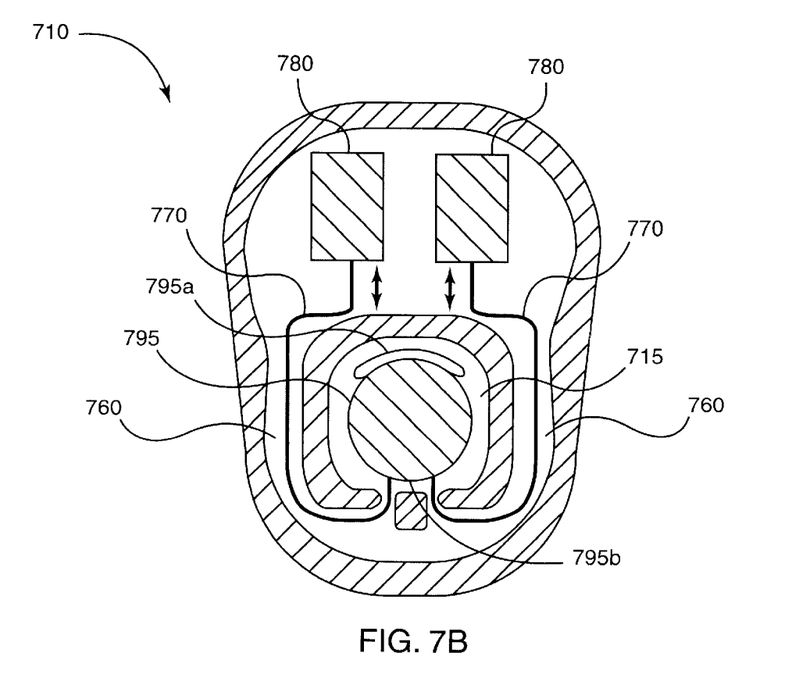

FIGS. 7A and 7B are cross-sectional diagrams of yet another embodiment of stimulation system 200. Stimulation system 200 includes a glove-like stimuli device 700 with a plurality of finger stimuli rings 710, 720, 730, 740 and 750. Individual 290 inserts the fingers of a hand into the respective holes 715, 725, 735, 745 and 755 of stimuli rings 710, 720, 730, 740 and 750.

FIG. 7B is a detailed cross sectional diagram of one of the stimuli rings, e.g., stimuli ring 710. Note that a finger tip pad 795*b* of a finger tip segment 795 of a finger of individual 290 is resting on probes 770. Actuators 780 are operatively coupled to probes 770 and are guided by channels 760. Blunt probe tips of probes 770 are in contact with finger tip pad 795*b*. Stimuli is selectively provided to individual 290 by controlling actuators 780 which moves one or more of the blunt tips of probes 770 towards and away from pad 795*b*.

Note that actuators 780 are located on the back of the hand, i.e., on the nail 795*a* side of finger tip segment 795, in order to minimize the profile of the portion of stimuli ring 710 under finger pad 795b. Such an arrangement maximizes the freedom of movement that can be provided by glove-like stimuli device 700 to the fingers.

Feedback from individual 290 can be verbal, i.e., via a microphone, or via a motion of the finger(s). Accordingly, three-dimensional position sensing capability can be incorporated into glove-like stimuli device 700. An optional corresponding model of the hand can be displayed on monitor 104 of stimulation system 200, thereby providing visual cues to individual 290 during the training session. In addition, force feedback capability can also be incorporated into device 700. The position sensing, display and feedback capabilities are available from Virtual Technologies Inc. of Palo Alto, Calif. (see website www.virtex.com).

Many modifications are possible. For example, in a simplified embodiment of stimulation system 200, feedback is not required of individual 290, i.e., efficiency and the ability to monitor compliance can be traded off for simplicity of design and low cost. In addition, the training regimen described above is also applicable for remedial training, i.e., to avoid developing the motor control problem, e.g., focal dystonia. By starting treatment early, preventative use of the training regimen can prevent the destructive process of sensory integration before an observable motor control problem develops. The present invention is advantageous because the training regimen of the present invention addresses the root cause of the motor control problem. As such, motor control improvements resulting from the re-establishment of differential sensory ability should be substantial and long lasting.

While this invention has been described in terms of several preferred embodiments, there are alterations, permutations, and equivalents which fall within the scope of this invention. For example, while the above described RSI injuries involve the hand, such injuries can occur with another portion of the body, e.g., the feet. It is therefore intended that the following appended claims be interpreted as including all such alterations, permutations, and equivalents as fall within the true spirit and scope of the present invention.

What is claimed is:

1. A method for improving motor control of a portion of an individual with impaired motor control, the method using a system having a processor, a stimulator and an input device, the stimulator operatively coupled to the portion, the method comprising:
   a) selecting a first and second location from a plurality of locations within the portion, wherein the individual may have difficulty sensing differentially between the first and second locations;
   b) differentially stimulating said first and second location using the stimulator;
   c) receiving feedback from the individual via the input device, the feedback indicating the degree of difficulty the individual has in sensing differentially between the first and second locations; and
   d) adaptively repeating b by varying the stimuli based on the feedback from c, wherein the stimuli are adapted based on the feedback from the individual to improve sensing between the first and second locations.

2. The method of claim 1 further comprising:
   e) selecting a third location from the plurality of locations, the selection of the third location based on the feedback from c;
   f) differentially stimulating said first and third location using the stimulator;
   g) receiving feedback from the individual via the input device, the feedback indicating the degree of difficulty the individual has in sensing differentially between the first and third locations; and
   h) adaptively repeating f by varying the stimuli based on the feedback from g.

3. The method of claim 2 wherein the distance between the first and second location is greater than the distance between the first and third location.

4. The method of claim 2 wherein the distance between the first and second location is less than the distance between the first and third location.

5. The method of claim 1 wherein the motor control impairment of individual is associated with focal dystonia, neural injury or disease, or neglect during recovery.

6. The method of claim 5 wherein the focal dystonia is caused by repetitive strain injury (RSI).

7. The method of claim 1 wherein adapting d includes modifying the stimuli in b temporally or spectrally.

8. The method of claim 7 wherein the spectral modification of the stimuli includes a modification of an intensity or amplitude of the stimuli.

9. The method of claim 1 wherein motivational reward is provided to the individual to encourage the individual to attend to the stimuli.

10. The method of claim 1 wherein the stimuli is somatosensory, proprioceptive or kinesthetic.

11. The method of claim 10 wherein the somatosensory stimuli includes tactile, pressure or textural stimulation.

12. A sensory stimulation system for improving motor control of a portion of an individual with impaired motor control comprising:
   a processor configured to select a first and second location from a plurality of locations within the portion, wherein the individual may have difficulty sensing differentially between the first and second locations;
   a stimulator operatively coupled to the portion and configured to differentially stimulate said first and second location; and
   an input device configured to receive feedback from the individual via the input device, the feedback indicating the degree of difficulty the individual has in sensing differentially between the first and second locations, and wherein the processor is further configured to adaptively vary the stimuli based on the feedback from the individual to improve sensing between the first and second locations.

13. The stimulation system of claim 12 wherein:
   the processor is further configured to select a third location from the plurality of locations, the selection of the third location based on the feedback from the individual;
   the stimulator is further configured to differentially stimulate said first and third location; and
   the input device is further configured to receive feedback from the individual, the feedback indicating the degree of difficulty the individual has in sensing differentially between the first and third locations; and wherein the stimulator adaptively varies the stimuli based on the feedback from the individual.

14. The stimulation system of claim 13 wherein the distance between the first and second location is greater than the distance between the first and third location.

15. The stimulation system of claim 13 wherein the distance between the first and second location is less than the distance between the first and third location.

16. The stimulation system of claim 12 wherein the motor control impairment of individual is associated with focal dystonia, neural injury or neural disease.

17. The stimulation system of claim 16 wherein the focal dystonia is caused by repetitive strain injury (RSI).

18. The stimulation system of claim 12 wherein the stimulator adaptively modifies the stimuli on the first and second location temporally or spectrally.

19. The stimulation system of claim 18 wherein the spectral modification of the stimuli includes a modification of an intensity or amplitude of the stimuli.

20. The stimulation system of claim 12 wherein motivational reward is provided to the individual to encourage the individual to attend to the stimuli.

21. The stimulation system of claim 12 wherein the stimuli is somatosensory, proprioceptive or kinesthetic.

22. The stimulation system of claim 21 wherein the somatosensory stimuli includes tactile, pressure or textural stimuli.

23. A computer program product including a computer-usable medium having computer-readable code embodied therein, the computer program product useful in association with a sensory stimulation system for improving motor control of a portion of an individual with impaired motor control, the stimulation system having a processor, a stimulator and an input device, the stimulator operatively coupled to the portion of the individual, the computer program product comprising:

computer-readable code configured to cause the processor to select a first and second location from a plurality of locations within the portion, wherein the individual may have difficulty sensing differentially between the first and second locations;

computer-readable code configured to cause the stimulator to differentially stimulate said first and second location;

computer-readable code configured to cause the input device to receive feedback from the individual, the feedback indicating the degree of difficulty the individual has in sensing differentially between the first and second locations; and computer-readable code configured to cause the processor to adaptively vary the stimuli based on the feedback from the individual to improve sensing between the first and second locations.

24. The computer program product of claim 23 further comprising:

computer-readable code configured to cause the processor to select a third location from the plurality of locations, the selection of the third location based on the feedback from the individual;

computer-readable code configured to cause the stimulator to differentially stimulate said first and third location;

computer-readable code configured to cause the input device to receive feedback from the individual, the feedback indicating the degree of difficulty the individual has in sensing differentially between the first and third locations; and computer-readable code configured to cause the stimulator to adaptively vary the stimuli based on the feedback from the individual.

25. The computer program product of claim 24 wherein the distance between the first and second location is greater than the distance between the first and third location.

26. The computer program product of claim 24 wherein the distance between the first and second location is less than the distance between the first and third location.

27. The computer program product of claim 23 wherein the motor control impairment of individual is associated with focal dystonia neural injury or neural disease.

28. The computer program product of claim 27 wherein the focal dystonia is caused by repetitive strain injury (RSI).

29. The computer program product of claim 23 wherein the stimulator adaptively varies the stimuli temporally or spectrally.

30. The computer program product of claim 29 wherein the spectral modification of the stimuli includes a modification of an intensity or amplitude of the stimuli.

31. The computer program product of claim 23 wherein motivational reward is provided to the individual to encourage the individual to attend to the stimuli.

32. The computer program product of claim 23 wherein the stimuli is somatosensory, proprioceptive or kinesthetic.

33. The computer program product of claim 32 wherein the somatosensory stimulation includes tactile, pressure or textural stimuli.

* * * * *